(12) United States Patent
Terumoto

(10) Patent No.: US 9,913,586 B2
(45) Date of Patent: Mar. 13, 2018

(54) PULSE WAVE SENSOR

(71) Applicant: Rohm Co., Ltd., Kyoto (JP)

(72) Inventor: Koji Terumoto, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 452 days.

(21) Appl. No.: 14/629,959

(22) Filed: Feb. 24, 2015

(65) Prior Publication Data

US 2015/0238099 A1  Aug. 27, 2015

(30) Foreign Application Priority Data

Feb. 25, 2014  (JP) .................................. 2014-034279

(51) Int. Cl.
   *A61B 5/024*  (2006.01)
   *A61B 5/00*  (2006.01)

(52) U.S. Cl.
   CPC ........ *A61B 5/02444* (2013.01); *A61B 5/0059* (2013.01); *A61B 5/681* (2013.01)

(58) Field of Classification Search
   CPC .... A61B 5/0059; A61B 5/02444; A61B 5/681
   See application file for complete search history.

(56) References Cited

U.S. PATENT DOCUMENTS 7,388,660 B2 * 6/2008 Kobayashi ................ G01J 1/04
356/222

FOREIGN PATENT DOCUMENTS

JP  05-161615  6/1993

* cited by examiner

*Primary Examiner* — Michael Rozanski
(74) *Attorney, Agent, or Firm* — Fish & Richardson P.C.

(57) ABSTRACT

A pulse wave sensor includes: a light emitting unit configured to emit light onto a living body; a light receiving unit configured to receive light transmitted through or reflected from the living body based on the light from the light emitting unit; a pulse wave detecting unit configured to detect a pulse wave of the living body based on a result of light reception by the light receiving unit when the light is emitted from the light emitting unit with a normal light emission intensity; and a light emission intensity adjusting unit configured to cause the light emitting unit to emit light with a predetermined test light emission intensity in a test period prior to the detection of the pulse wave, and set the normal light emission intensity using detection light reception intensity in the light receiving unit by the light emission and a predetermined reference light reception intensity.

19 Claims, 13 Drawing Sheets

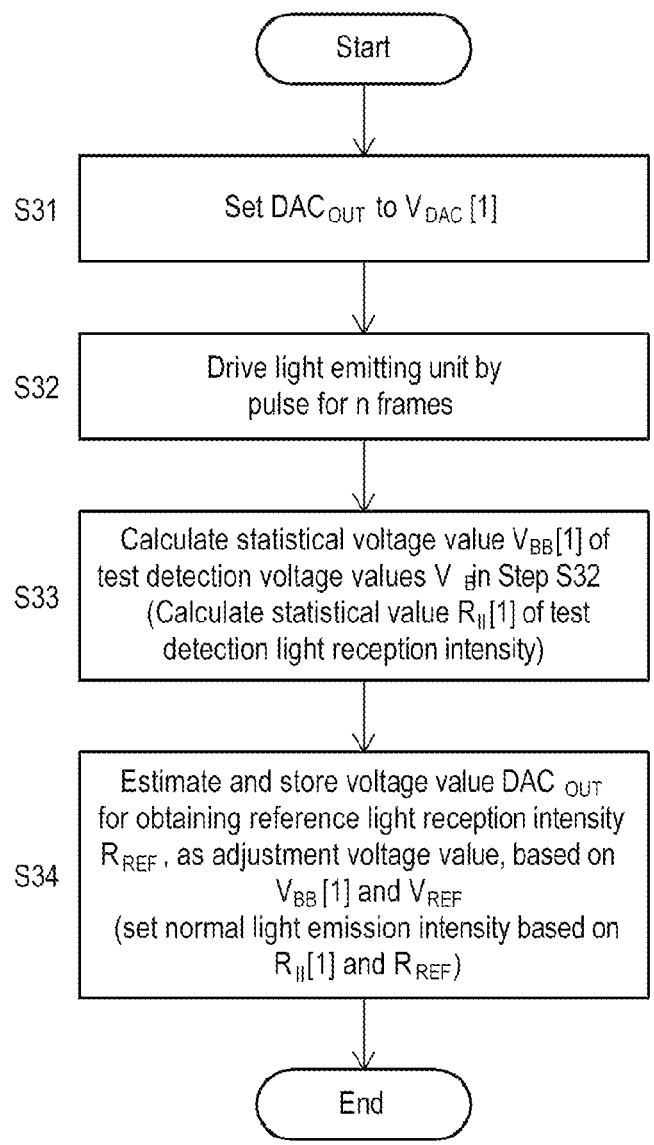

PULSE WAVE SENSOR

CROSS-REFERENCE TO RELATED APPLICATION

This application is based upon and claims the benefit of priority from Japanese Patent Application No. 2014-034279, filed on Feb. 25, 2014, the entire contents of which are incorporated herein by reference.

TECHNICAL FIELD

The present disclosure relates to a pulse wave sensor.

BACKGROUND

A conventional pulse sensor for detecting a pulse wave of a living body based on a light receiving signal of light, which is transmitted through the living body when the living body is emitted with light from a light emitting unit, has been known. In such a pulse wave sensor, since an intensity of the received light varies with a pulsation of the living body, pulse wave information (e.g., a heart rate of the living body, etc.) can be obtained based on characteristics of the pulse wave signal (e.g., a fluctuation cycle of the pulse wave signal, etc.) corresponding to the intensity of the received light.

An amplitude of the pulse wave signal depends on a light emission intensity of the light emitting unit. However, if the amplitude of the pulse wave signal becomes too small as the light emission intensity is small, it may become difficult to obtain accurate pulse wave information. On the other hand, if the light emission intensity becomes too large in order to increase the amplitude of the pulse wave signal, it may also become difficult to obtain accurate pulse wave information due to saturation of the pulse wave signal. Thus, in order to obtain the accurate pulse wave information, it is necessary to optimize the amplitude of the pulse wave signal. If there are no individual differences in attenuations (i.e., light absorbances) of light in living bodies, the light emission intensity required to obtain proper amplitude of the pulse wave signal is uniquely determined. However, there may be differences among attenuations of individuals. In addition, an attenuation may vary each time for the same person depending on how to install the pulse wave sensor, etc.

A following amplitude detection method may be considered as one of methods for optimizing an amplitude of a pulse wave signal. The amplitude detection method includes directly reading amplitudes of the pulse wave signal (i.e., a difference between the maximum signal value and the minimum signal value) by emitting light with a test light emission intensity from a light emitting unit before an actual detection period during which a pulse wave is actually detected, and then setting a light emission intensity in the actual detection period (i.e., a normal light emission intensity) based on the read amplitudes. If the cycle of pulse wave is 1 Hz, in order to directly read an amplitude of the pulse wave signal with a single test light emission intensity, it takes at least one second, generally two to three seconds to ensure some degrees of accuracy. In addition, in order to provide a high-accurate setting of the light emission intensity (i.e., the normal light emission intensity) in the actual detection period, directly sequentially reading amplitudes of the pulse wave signal (i.e., a difference between the maximum signal value and the minimum signal value) by sequentially emitting light with a plurality of different test light emission intensities from light emitting unit, and then setting the light emission intensity in the actual detection period (i.e., the normal light emission intensity) based on the plurality of read amplitudes may be also contemplated. In this case, a required time may be equal to "(the number of types of test light emission intensities)×2" through "(the number of types of test light emission intensities)×3."

When an adjustment process for amplitude optimization is performed, i.e., when an adjustment process for optimization of light emission intensity is performed, actual pulse wave detection is not performed. Thus, a shorter time required for the adjustment process is better.

SUMMARY

The present disclosure provides some embodiments of a pulse wave sensor, which is capable of achieving optimization of light emission intensity for use in detecting a pulse wave in a short time.

According to one embodiment of the present disclosure, there is provided a pulse wave sensor including: a light emitting unit configured to emit light onto a living body; a light receiving unit configured to receive light, which is transmitted through or is reflected from the living body based on the light from the light emitting unit; a pulse wave detecting unit configured to detect a pulse wave of the living body based on a result of light reception by the light receiving unit when the light is emitted from the light emitting unit with a normal light emission intensity; and a light emission intensity adjusting unit configured to cause the light emitting unit to emit light with a predetermined test light emission intensity in a test period prior to the detection of the pulse wave, and set the normal light emission intensity using a detection light reception intensity in the light receiving unit by the light emission and a predetermined reference light reception intensity.

In some embodiments, the light emission intensity adjusting unit is configured to cause the light emitting unit to sequentially emit light with a plurality of different test light emission intensities in the test period, and set the normal light emission intensity using a plurality of detection light reception intensities in the light receiving unit that correspond to the plurality of test light emission intensities and the predetermined reference light reception intensity.

In some embodiments, the light emission intensity adjusting unit is configured to implement sequential light emission with the plurality of test light emission intensities according to a process of increasing the light emission intensity of the light emitting unit stepwise, and set the normal light emission intensity based on the test light emission intensity before or after the detection light reception intensity is switched from below the reference light reception intensity to the reference light reception intensity or more in the course of the process of increasing the light emission intensity, or the light emission intensity adjusting unit is configured to implement sequential light emission with the plurality of test light emission intensities according to a process of decreasing the light emission intensity of the light emitting unit stepwise, and set the normal light emission intensity based on the test light emission intensity before or after the detection light reception intensity is switched from above the reference light reception intensity to the reference light reception intensity or less in the course of the process of decreasing the light emission intensity.

In some embodiments, the light emission intensity adjusting unit is configured to first cause the light emitting unit to emit light with a smallest one of the plurality of test light emission intensities, stop the process of increasing the light emission intensity when the detection light reception intensity is equal to or larger than the reference light reception intensity, and set the normal light emission intensity based on the smallest test light emission intensity, or the light emission intensity adjusting unit is configured to first cause the light emitting unit to emit light with a greatest one of the plurality of test light emission intensities, stop the process of decreasing the light emission intensity when the detection light reception intensity is equal to or less than the reference light reception intensity, and sets the normal light emission intensity based on the greatest test light emission intensity.

In some embodiments, the light emission intensity adjusting unit is configured to estimate a light emission intensity for obtaining the reference light reception intensity based on the plurality of detection light reception intensities and the reference light reception intensity, and set the normal light emission intensity based on the estimated light emission intensity.

In some embodiments, the test light emission intensity is a predetermined single light emission intensity, and the light emission intensity adjusting unit is configured to set the normal light emission intensity based on a result of comparison between the detection light reception intensity and the reference light reception intensity.

In some embodiments, the length of a period, during which light is emitted from the light emitting unit with each of the plurality of test light emission intensities, is set to be shorter than the cycle of the pulse wave or is set to 0.5 second or less.

In some embodiments, a total length of periods, during which light is emitted from the light emitting unit with the plurality of test light emission intensities, is set to be shorter than the cycle of the pulse wave or is set to 0.5 second or less.

In some embodiments, a length of a period, during which light is emitted from the light emitting unit with the test light emission intensity is set to be shorter than the cycle of the pulse wave or is set to 0.5 second or less.

In some embodiments, the light emission intensity adjusting unit is configured to turn on the light emitting unit by pulse with the test light emission intensity in the test period.

BRIEF DESCRIPTION OF THE DRAWINGS

FIG. 11 illustrates a comparative table between a regular turning-on and a pulse turning-on.

FIG. 14 illustrates a flowchart of an adjustment process according to a third embodiment of the present disclosure.

DETAILED DESCRIPTION

Figure 1:
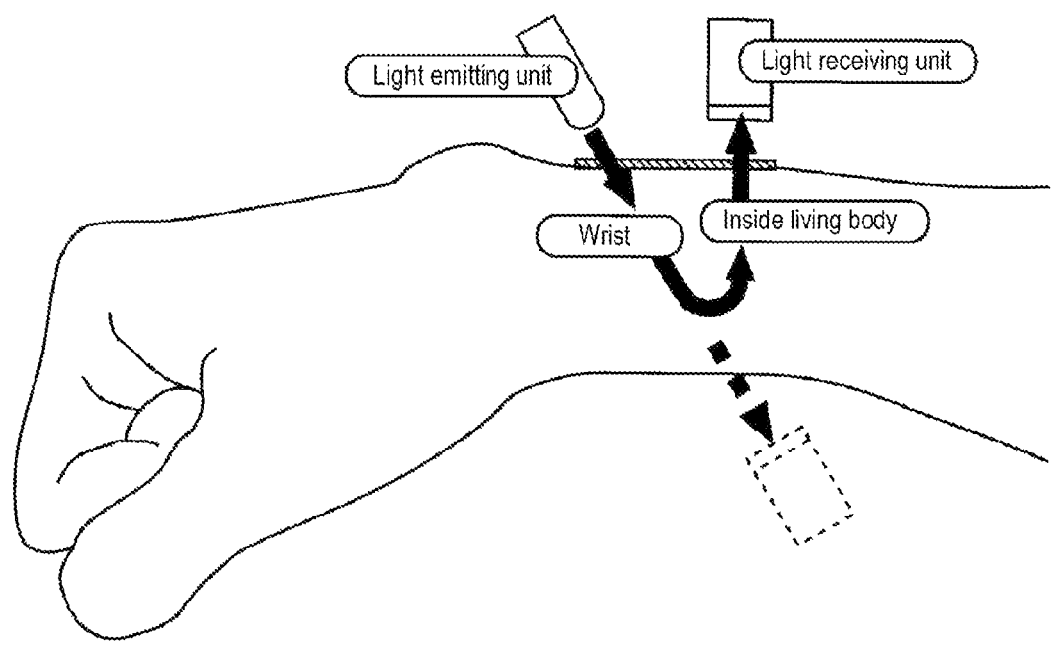
FIG. 1 illustrates a schematic view for showing a principle of pulse wave measurement in a wrist.

Exemplary embodiment of the present disclosure will now be described in detail with reference to the drawings. Throughout the drawings, the same elements are denoted by the same reference numerals and explanation for the same elements will not be repeated in principle. In the specification, for simplification of description, by appending symbols or signs to information, signals, physical quantities, state quantities, members, or the like, names of the information, signals, physical quantities, state quantities, members, or the like, corresponding to the symbols and signs may be omitted or abbreviated. In addition, a plurality of processes in any plurality of steps in any flowcharts as will be described later may be executed in any execution order or in parallel, unless contradictory.

<<Principle of Pulse Wave Measurement>>

Figure 2:
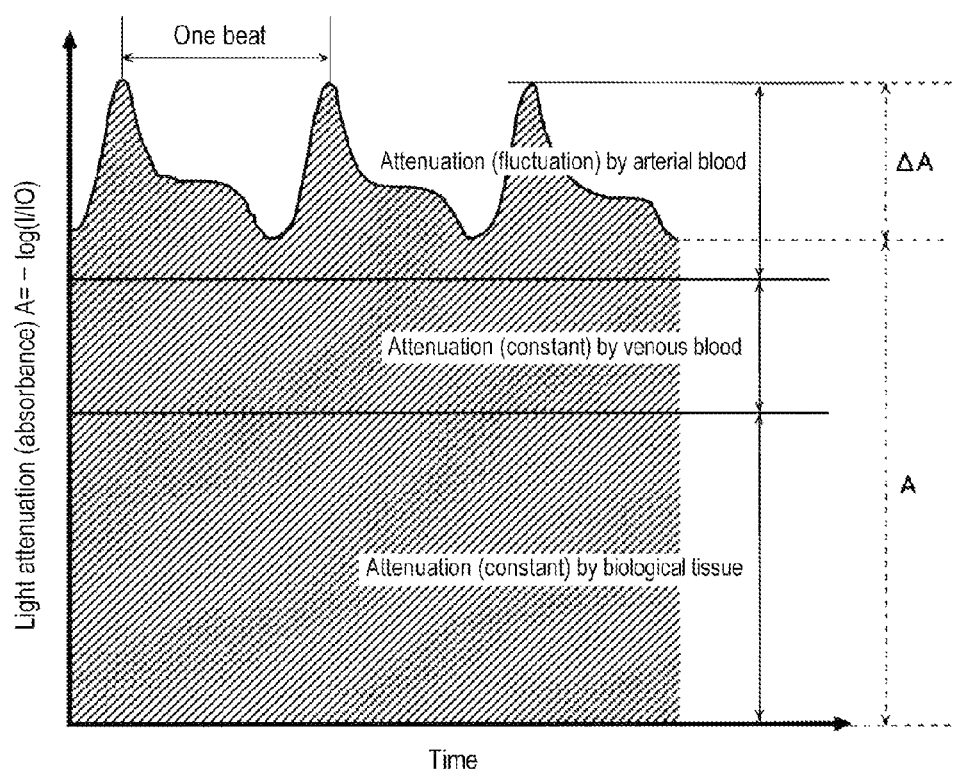
FIG. 2 illustrates a waveform diagram showing temporal changes in light attenuation mounts in a living body.

FIG. 1 illustrates a schematic view for showing a principle of pulse wave measurement in a wrist and FIG. 2 illustrates a waveform diagram showing temporal changes in light attenuations (i.e., absorbances) in a living body. In embodiments to be described later, pulse wave measurement is performed based on the principle described below.

In pulse wave measurement using a volume pulse wave method, for example, as shown in FIG. 1, light is emitted from a light emitting unit (such as an LED (Light Emitting Diode) or the like) toward a part (a wrist in FIG. 1) of a living body, which is pressed on a measurement window, and is transmitted through the inside of the wrist. An intensity of the light coming out of the wrist is detected in a light receiving unit, such as a photo diode, a photo transistor, or the like. In this case, as shown in FIG. 2, light attenuation (i.e., an absorbance) by biological tissues or venous blood (deoxygenated hemoglobin (Hb)) is constant while light attenuation (i.e., an absorbance) by arterial blood (oxygenated hemoglobin (HbO2)) is varied with time by pulsation. Accordingly, by measuring a change in absorbances of arterial blood based on the a result of light reception of the light receiving unit using a "biological window" (a wavelength range, in which light can easily be transmitted through a living body) ranging from a visible region range to a near-infrared region, it is possible to measure a volume pulse wave in non-invasive conditions.

In addition, for convenience of illustration, although it is depicted in FIG. 1 that the pulse wave sensor having the light emitting unit and the light receiving unit is mounted on a back side (i.e., outer side) of the wrist, the mounting position of the pulse wave sensor is not limited thereto but the pulse wave sensor may be mounted on a ventral side (i.e., inner side) of the wrist or other sides such as finger tips, a third joint of the finger, a forehead, an area between the eyebrows, a nose tip, a cheek, under eyes, a temple, an ear lobe, a sear hole or the like.

The pulse wave under the rule of heart and autonomic nerve does not always indicate a certain behavior but undergoes various changes (e.g., fluctuations) based on conditions of a subject. Thus, a variety of body information of the subject can be obtained by analyzing the changes (e.g., fluctuations) of the pulse wave. For instance, an exercise capacity, a level of tension, etc. of the subject may be obtained from a heart rate of the subject and a fatigue, a sleep degree, a magnitude of stress, and the like of the subject may be obtained from heart rate variability of the subject. In addition, a vascular age, a degree of arteriosclerosis, etc. of the subject may be obtained from an acceleration pulse wave obtained by differentiating the pulse wave twice on a time axis.

<<First Embodiment>>

Figure 3:
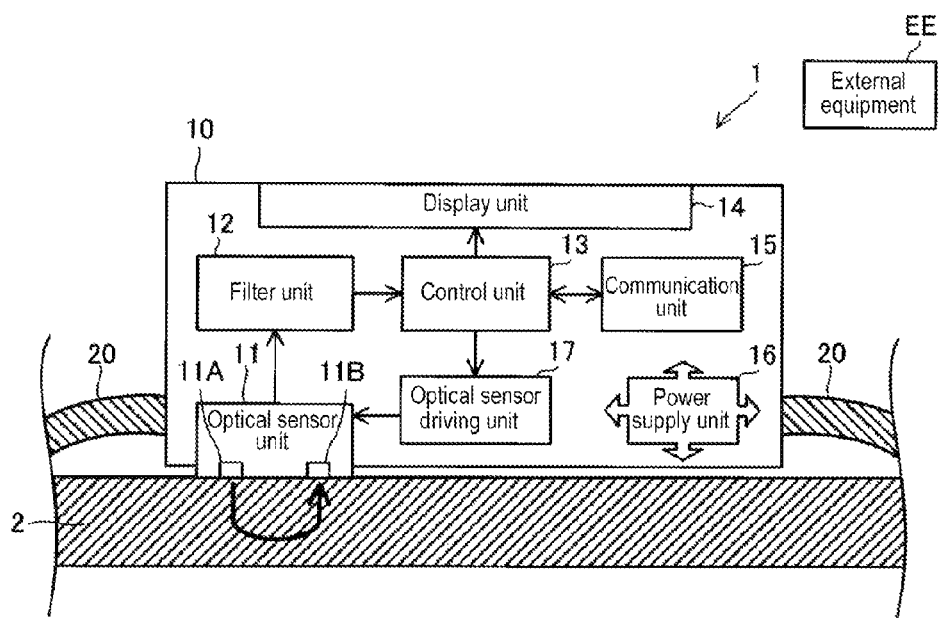
FIG. 3 illustrates a block diagram of a pulse wave sensor according to a first embodiment of the present disclosure.

A first embodiment of the present disclosure will now be described. FIG. 3 illustrates a block diagram showing a pulse wave sensor 1 according to the first embodiment, along with a living body 2 and an external equipment EE. The pulse wave sensor 1 has a bracelet structure (wrist watch type structure) including a body unit 10 and a belt 20, which is attached to both ends of the body unit 10 and is wound around the living body 2 (e.g., a wrist). The belt 20 may be made of leather, metal, resin or the like. As used herein, a subject may refer to a human with the living body 2.

The body unit 10 includes an optical sensor unit 11, a filter unit 12, a control unit 13, a display unit 14, a communication unit 15, a power supply unit 16 and an optical sensor driving unit 17.

The optical sensor unit 11 is formed on the rear surface (i.e., a surface facing the living body 2) of the body unit 10 and includes a light emitting unit 11A such as an LED, etc., and a light receiving unit 11B. The optical sensor unit 11 may obtain a pulse wave signal by emitting light from the light emitting unit 11A onto the living body 2 and detecting an intensity of light, which is transmitted through the inside of the living body 2, the inside of the emitted light, by means of the light receiving unit 11B. Although a reflection type structure, as indicated by a solid arrow in FIG. 1, where the light emitting unit 11A and the light receiving unit 11B are both disposed in the same side with respect to the living body 2 is employed in this embodiment, a transmission type structure, as indicated by a dashed arrow in FIG. 1, where the light emitting unit 11A and the light receiving unit 11B are disposed in the opposite sides with the living body 2 interposed therebetween may be employed. Specifically, in the reflection type structure, light is emitted from the light emitting unit 11A onto the living body 2, and light, which is transmitted through a portion of the living body 2, the inside of the emitted light and is then reflected into the inside of the living body 2, is received in the light receiving unit 11B. On the other hand, in the transmission type structure, light is emitted from the light emitting unit 11A onto one side of the living body 2 and light, which is transmitted through the living body 2, the inside of the emitted light, and is then emitted from the other side (in the opposite to the one side) of the living body 2, is received in the light receiving unit 11B. In sum, the light receiving unit 11B may receive light, which is transmitted through or is reflected from the living body 2, on the basis of light emitted from the light emitting unit 11A.

The filter unit 12 performs a filtering process and an amplifying process on an output signal of the optical sensor unit 11, and transfers the filtered and amplified signal to the control unit 13. The control unit 13 controls the entire operation of the pulse wave sensor 1 overall, and further obtains various information related to the pulse wave (hereinafter referred to as pulse wave information) by performing various kinds of signal processing on an output signal of the filter unit 12. The pulse wave information may include, for example, a heart rate, a fluctuation of the pulse wave, a heart rate variability, and an acceleration of the pulse wave. The control unit 13 may be implemented with a Micro Processing Unit (MPU), etc. The display unit 14, which is formed of a liquid crystal panel, etc. disposed on the front surface (a surface, which does not face the living body 2) of the body unit 10, displays display information including the pulse wave information, information related to date and time, etc. The display unit 14 may correspond to a letter board of a wrist watch. The communication unit 15 performs any communication between the pulse wave sensor 1 and the external equipment EE. The communication unit 15 can wirely or wirelessly transmit measurement data of the pulse wave sensor 1 including the pulse wave information to the external equipment EE. The external equipment EE is any electronic equipment such as a personal computer, a mobile phone or the like and may be connected to the communication unit 15 via a network. The power supply unit 16 includes a battery and a DC/DC converter and converts an input voltage from the battery into a desired output voltage, which is then supplied to the respective units of the pulse wave sensor 1. The optical sensor driving unit 17 drives the optical sensor unit 11 under control of the control unit 13.

Figure 4:
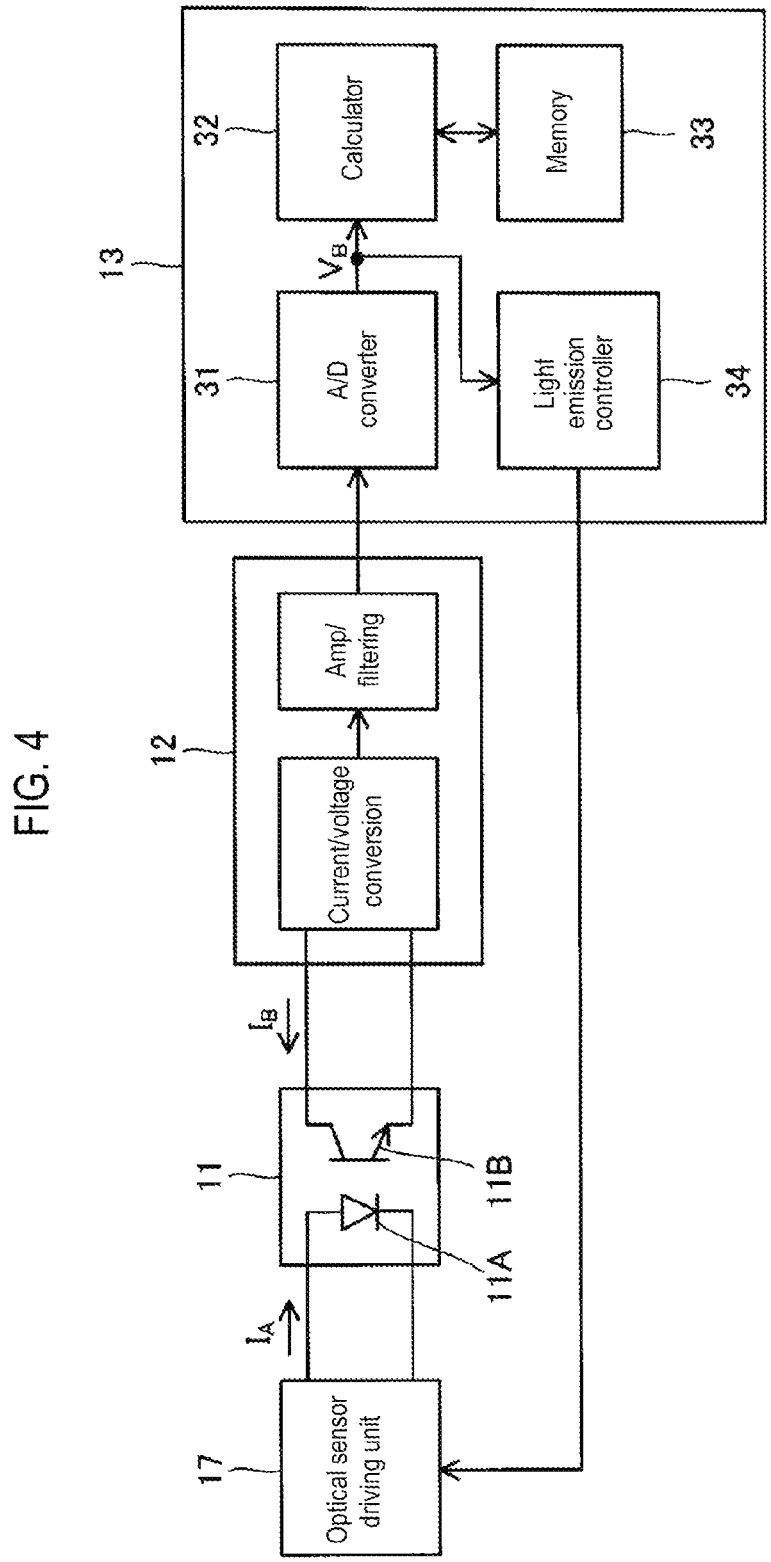
FIG. 4 illustrates a block diagram of a relationship among an optical sensor unit, a filter unit, a control unit, and an optical sensor driving unit, along with a circuit example of the optical sensor unit, according to the first embodiment of the present disclosure.

FIG. 4 shows a relationship among the optical sensor unit 11, the filter unit 12, the control unit 13, and the optical sensor driving unit 17, along with a circuit example of the optical sensor unit 11. The control unit 13 includes an A/D converter 31, a calculator 32, a memory 33 and a light emission controller 34.

When a driving current $I_A$ is supplied from the optical sensor driving unit 17 into the light emitting unit 11A formed of an LED, the light emitting unit 11A emits light accordingly. The transmitted light based on the light emission of the light emitting unit 11A is received in the light receiving unit 11B formed of a photo transistor, and a current $I_B$ according to an intensity of the received light (hereinafter referred to as a light receiving current) is flown in the light receiving unit 11B. A light emission intensity of the light emitting unit 11A increases with increase of the driving current $I_A$ in approximate proportion to the driving current $I_A$. The light receiving current $I_B$ increases with increase of received light intensity of the light receiving unit 11B in approximate proportion to the received light intensity. The "intensity" in the light emission intensity and the light receiving intensity may be any physical quantity indicative of an intensity of light, for example, an illuminance, a luminous flux, a luminous intensity or a brightness. Hereinafter, a light emission and a light receiving indicate light emission in the light emitting unit 11A and light receiving in the light receiving unit 11B, respectively, unless described specifically otherwise.

The filter unit 12 inputs an analog voltage signal, which may be obtained by converting a current signal indicative of a waveform of the light receiving current $I_B$ into a voltage signal and performing a filtering process and an amplifying process on the voltage signal, to the A/D converter 31. The A/D converter 31 converts the analog voltage signal into a digital voltage signal to be output. The input analog voltage signal and the output digital voltage signal of the A/D converter 31 are a kind of a pulse wave signal indicative of a pulse wave of the living body 2 and have a waveform according to a waveform of the light receiving current $I_B$. A voltage having a value of the pulse wave signal (i.e., a pulse wave signal voltage) is denoted by a symbol "$V_B$." Although it is shown in FIG. 4 that an output signal value of the A/D converter 31 corresponds to the voltage $V_B$, a voltage having an input signal value of the A/D converter 31 may correspond to the voltage $V_B$ or a voltage in the filter unit 12 based on the light receiving current $I_B$ may be captured as the voltage $V_B$.

The calculator 32 generates the pulse wave information by performing various calculation processes on the pulse wave signal output from the A/D converter 31. The memory 33 includes a program memory for storing programs specifying processes executed by the calculator 32 and a data memory temporarily for storing a variety of data used or calculated by the calculator 32. The light emission controller 34 performs light emission control of the light emitting unit 11A through control of the optical sensor driving unit 17, while appropriately using the output signal of the A/D converter 31. The light emission control includes control of the light emission intensity and a light emission timing of the light emitting unit 11A. In addition, the light emission controller 34 may be contained in the calculator 32.

Figure 5:
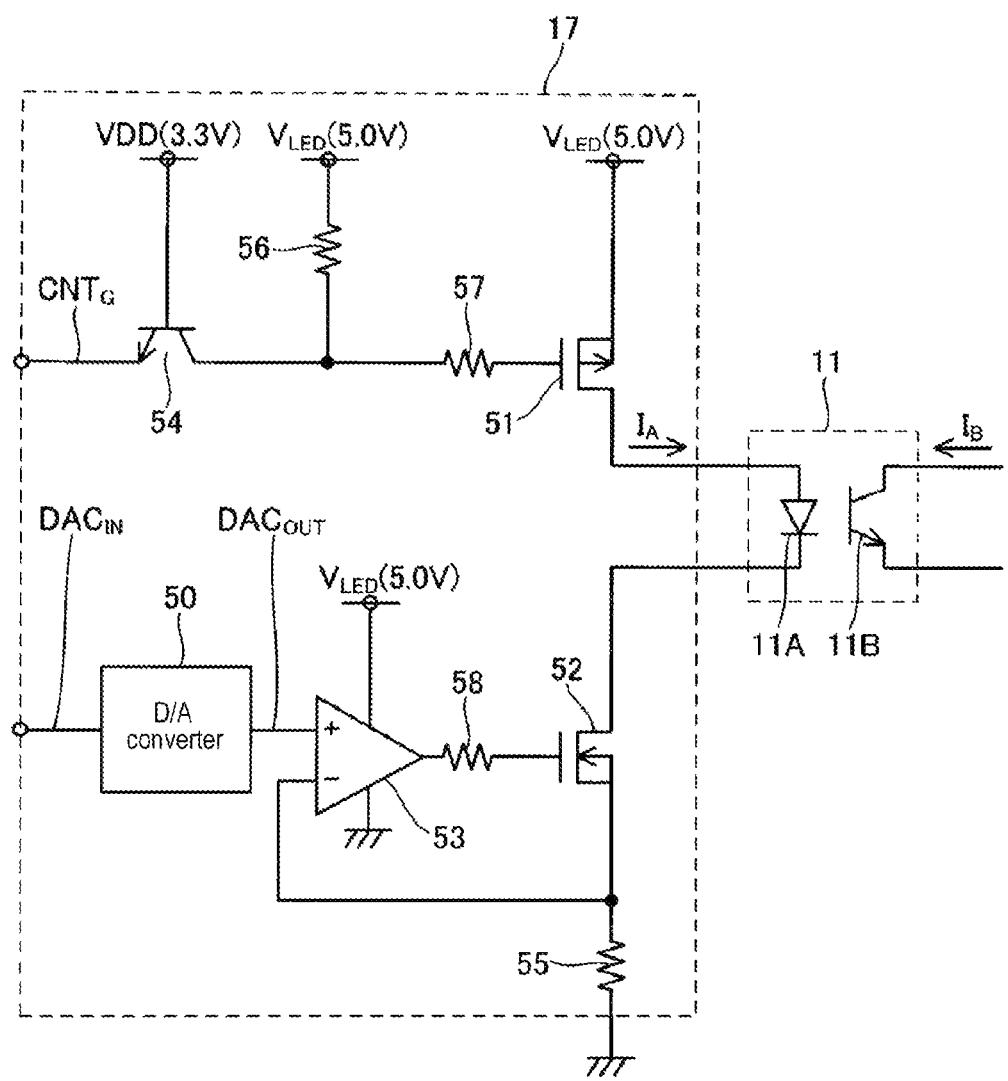
FIG. 5 illustrates an internal circuit example of the optical sensor driving unit.

FIG. 5 shows a circuit example of the optical sensor driving unit 17. The optical sensor driving unit 17 of FIG. 5 includes a D/A converter 50, a P channel type field effect transistor (FET) 51, an N channel type field effect transistor (FET) 52, an amplifier 53, an NPN bipolar transistor 54, and resistors 55 to 58. The transistor 54 may be a so-called digital transistor.

A predetermined positive DC voltage $V_{LED}$ (for example, 5 V) is applied to a source of the FET 51. In the LED as the light emitting unit 11A, an anode is connected to a drain of the FET 51 and a cathode is connected to a drain of the FET 52. A source of the FET 52 is connected to a reference potential point of 0V via the resistor 55 and a node between the source of the FET 52 and the resistor 55 is connected to an inverted input terminal of the amplifier 53. A predetermined positive DC voltage $V_{DD}$ (for example, 3.3 V) as a power supply voltage of the control unit 13 is applied to a base of the transistor 54. A control signal $CNT_G$ is supplied from the light emission controller 34 to an emitter of the transistor 54. A collector of the transistor 54 is connected to one end of the pull-up resistor 56 and is connected to a gate of the FET 51 via the resistor 57 such that the DC voltage $V_{LED}$ is applied to the other end of the pull-up resistor 56.

The D/A converter 50 converts a control signal $DAC_{IN}$ supplied from the light emission controller 34 into an analog voltage $DAC_{OUT}$, which is then supplied to an non-inverted input terminal of the amplifier 53. An output terminal of the amplifier 53 is connected to a gate of the FET 52 via the resistor 58. Thus, when the FET 51 is turned on, a gate potential of the FET 52 is controlled in accordance with the analog voltage $DAC_{OUT}$ and the current IA having a current value of "$DAC_{OUT}/R_{55}$" (where, $R_{55}$ denotes a resistance of the resistor 55) is flown into the LED as the light emitting unit 11A. That is, the D/A converter 50, the amplifier 53, and the FET 52 form a constant current circuit for supplying a constant current $I_A$ to the light emitting unit 11A. The light emission controller 34 controls a value of the analog voltage $DAC_{OUT}$ by controlling a digital value of the control signal $DAC_{IN}$, thereby controlling a value of the constant current (and thus the light emission intensity). In addition, the light emission controller 34 turns on or off the FET 51 serving as a switch by controlling a potential of the control signal $CNT_G$. Additionally, the D/A converter 50 may be contained in the light emission controller 34.

Figure 6:
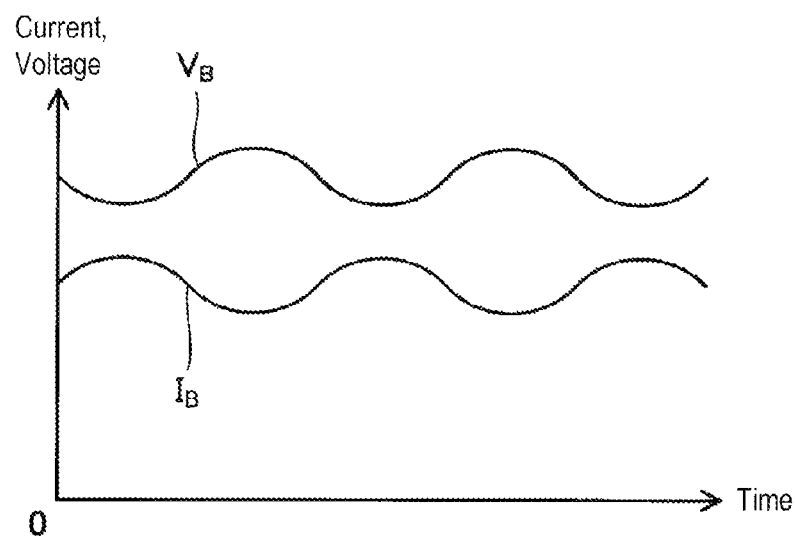
FIG. 6 illustrates waveforms of a light receiving current and a voltage depending on the light receiving current.

FIG. 6 shows waveforms of the light receiving current $I_B$ and the voltage (i.e., the pulse wave signal voltage) $V_B$, which are observed when light with constant light emission intensity is emitted from the light emitting unit 11A at all times. In this embodiment, although the circuit configuration where the voltage $V_B$ decreases with increase of the light receiving current $I_B$ whereas the voltage $V_B$ increases with decrease of the light receiving current $I_B$ is employed in the filter unit 12, a reverse circuit configuration may be employed in the filter unit 12.

If the amplitude of the pulse wave signal (i.e., the amplitude of the voltage $V_B$) becomes too small with decrease of the light emission intensity, it becomes difficult to obtain accurate pulse wave information. Further, even if the light emission intensity becomes too large so as to increase the amplitude of a pulse wave signal, the pulse wave signal exceeding a variable range of the voltage $V_B$ is provided and makes it difficult to obtain correct pulse wave information as well. Thus, amplitude optimization of the pulse wave signal is required to obtain accurate pulse wave information. If there is no individual difference in attenuation (i.e., an absorbance) of light, a light emission intensity required to obtain proper amplitude of the pulse wave signal may uniquely be determined. However, there may be differences among attenuations of individuals. In addition, an attenuation may vary each time for the same person depending on how to install the pulse wave sensor 1, etc. Therefore, prior to detection of a pulse wave, the light emission controller 34 performs an adjustment process for optimizing the amplitude of the pulse wave signal.

Figure 7:
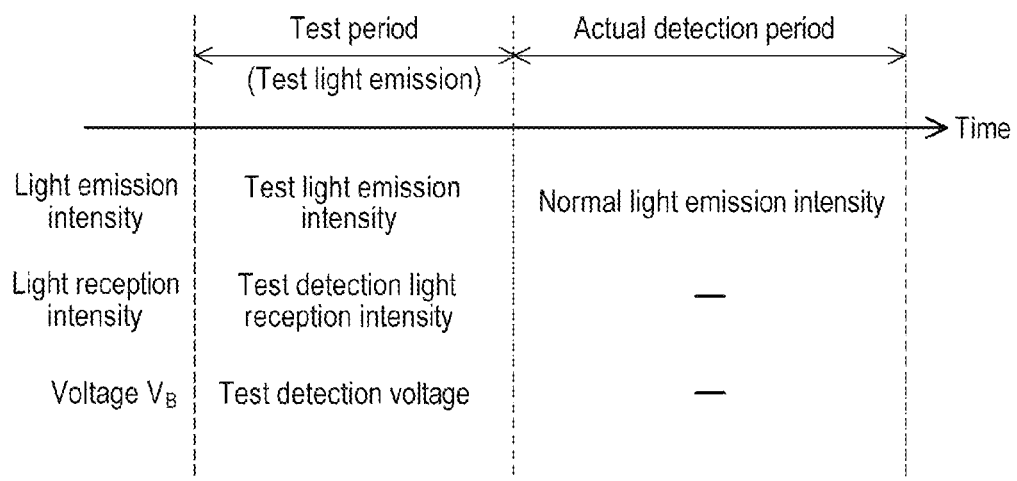
FIG. 7 illustrates a relationship between a test period and an actual detection period.

The adjustment process is performed in a test period, as shown in FIG. 7. Specifically, prior to an actual detection period where light with a normal light emission intensity is emitted from the light emitting unit 11A, the light emission controller 34 sets the test period where light with a test light emission intensity is emitted from the light emitting unit 11A. In the actual detection period, the control unit (particularly, the calculator 32) detects the pulse wave of the living body 2 based on a result of light reception of the light receiving unit 11B when the light with a normal light emission intensity is emitted from the light emitting unit 11A. The detection of the pulse wave includes acquisition of pulse wave information.

Referring to FIG. 7, a light emission with a test light emission intensity is referred to as "test light emission," a light receiving intensity of the light receiving unit 11B in the test light emission is referred to as "test detection light reception intensity," and the voltage $V_B$ by the light receiving current $I_B$ indicative of the test detection light reception intensity is referred to as "test detection voltage." The light emission controller 34 sets the normal light emission intensity based on the test detection light reception intensity. More specifically, since the test detection light reception intensity is indicated by the test detection voltage $V_B$, the light emission controller 34 sets the normal light emission intensity based on the test detection voltage $V_B$.

Figure 8:
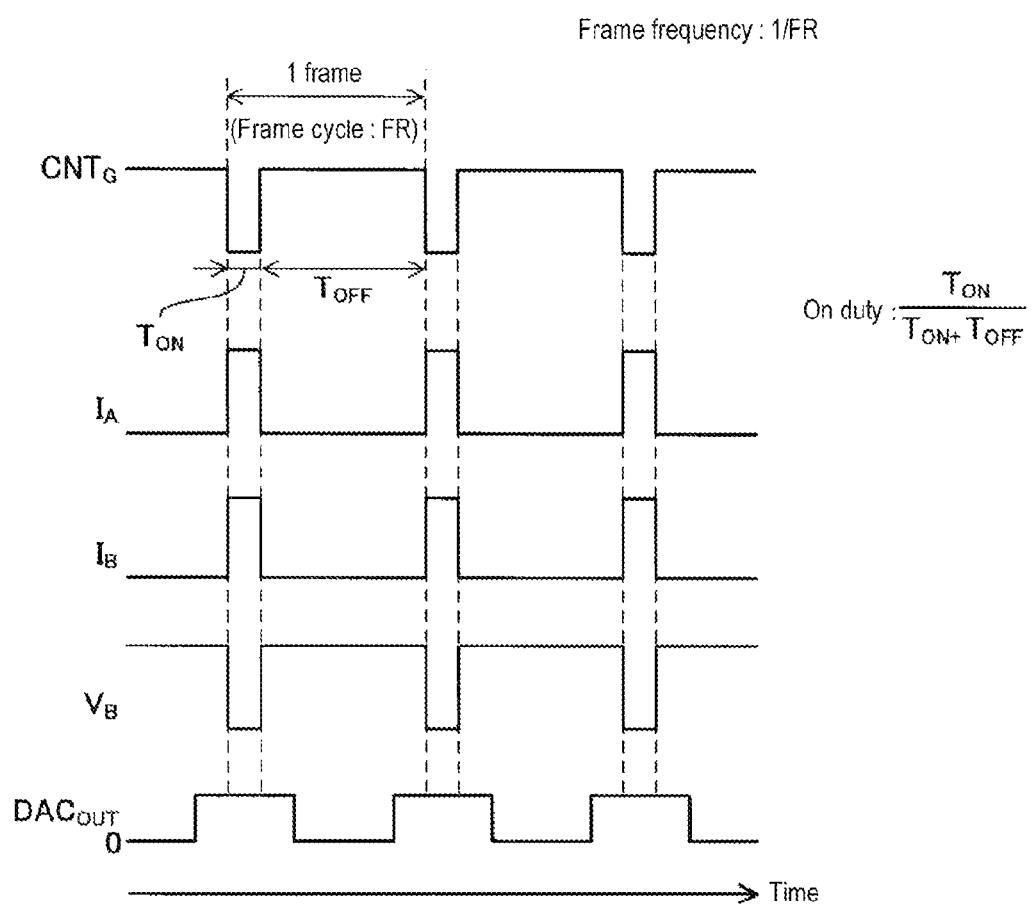
FIG. 8 illustrates waveforms of a control signal, a driving current of a light emitting unit, a light receiving current of a light receiving unit, a voltage depending on the light receiving current, and an output voltage of a D/A converter in pulse driving.

The light emission controller 34 turns on the light emitting unit 11A by driving the light emitting unit 11A by pulse in the test period. FIG. 8 shows waveforms of the control signal $CNT_G$, the driving current $I_A$, the light receiving current $I_B$, the voltage $V_B$, and the voltage $DAC_{OUT}$ in pulse driving. In the pulse driving, the light emission controller 34 repetitively performs unit processing, in which light is emitted only for time $T_{ON}$ but not only for time $T_{OFF}$ from the light emitting unit 11A by ON/OFF control of the FET 51 through a change of signal level of the control signal $CNT_G$. A unit period, during which the unit processing is performed, is referred to as "frame." The length of one frame corresponds to a frame cycle FR. A repetition frequency of the unit period, i.e., a frame frequency, is "1/FR." A relationship of "$FR=T_{ON}+T_{OFF}$" is established and a ratio "$T_{ON}/(T_{ON}+T_{OFF})$" is called "ON duty."

The frame frequency can be set to any frequency (e.g., 200 Hz). For example, the light emission controller 34 may select a frequency from a frequency range of 50 Hz to 1000 Hz as the frame frequency. The ON duty may be set to any value (e.g., 1/16). For example, the light emission controller 34 may select a value from a numerical range of 1/128 to 1/8 as the ON duty.

When the pulse driving is performed, as shown in FIG. 8, the light emission controller 34 may set the voltage $DAC_{OUT}$ to a desired voltage, which is larger than 0V, only in a period including the period in which the FET 51 is turned on, while setting the voltage $DAC_{OUT}$ to 0V in the remaining period (i.e., a period including all or some of the period in which the FET 51 is turned off without including the period in which the FET 51 is turned on). However, in the pulse driving, the voltage $DAC_{OUT}$ may be maintained at a desired voltage, which is larger than 0V, at all times. Hereinafter, voltage values of the voltages $V_B$ and $DAC_{OUT}$ are also referred to by "$V_B$" and "$DAC_{OUT}$," respectively.

Figure 9:
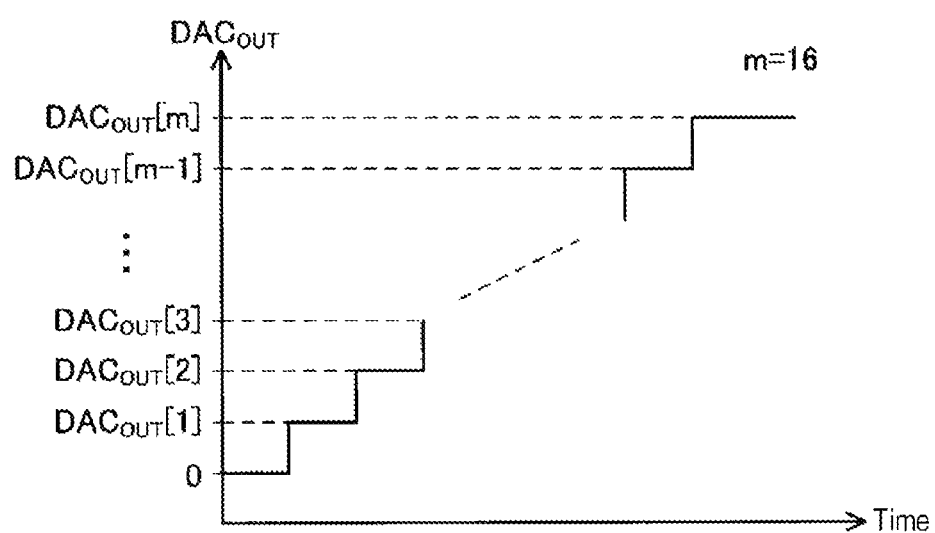
FIG. 9 illustrates a graph where the output voltage of the D/A converter increases stepwise.

The light emission controller 34 may assume any voltage falling within a range of voltage, which can be output by the D/A converter 50, as the voltage $DAC_{OUT}$. Voltage values of the voltage $DAC_{OUT}$ include predetermined voltage values $DAC_{OUT}[1]$ to $DAC_{OUT}[m]$, as shown in FIG. 9. The voltage value $DAC_{OUT}[1]$ is larger than 0 V. For any integer i, the voltage value $DAC_{OUT}[i+1]$ is larger than the voltage value $DAC_{OUT}[i]$. In the test period, as shown in FIG. 9, the light emission controller 34 can increase the voltage value $DAC_{OUT}$ stepwise from the voltage value $DAC_{OUT}[1]$ to the voltage value $DAC_{OUT}[m]$ (where m may be any integer of 2 or more). For example, m may be any integer falling within a range of 2 to 16. In this embodiment, m is 16.

Figure 10:
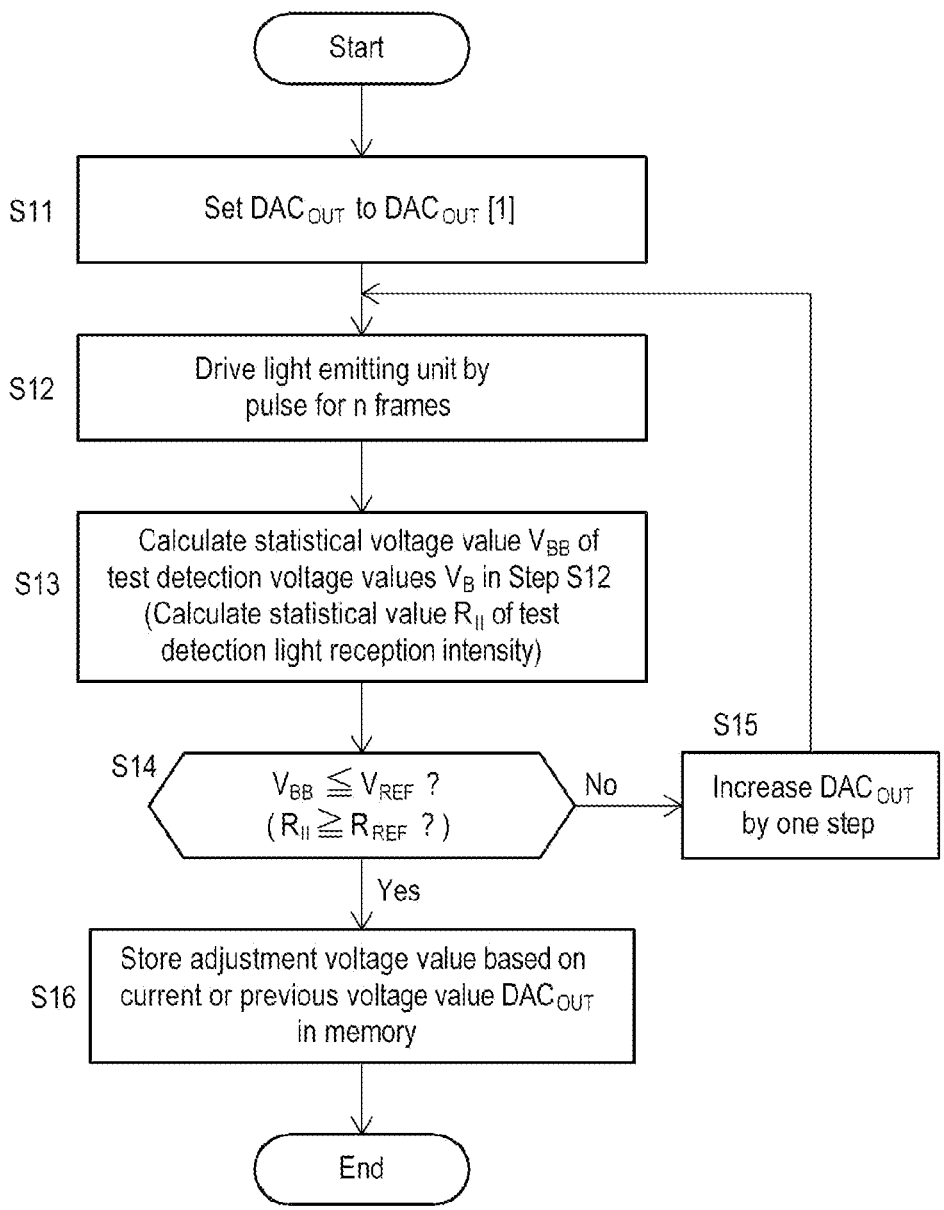
FIG. 10 illustrates a flowchart of an adjustment process according to the first embodiment of the present disclosure.

A procedure of the above-described adjustment process, which is also referred to as an amplitude adjustment process or a light emission intensity adjustment process, will now be described with reference to FIG. 10. FIG. 10 is a flowchart of the adjustment process. The adjustment process in the test period includes Steps S11 to S16.

The light emission controller 34 sets the output voltage value $DAC_{OUT}$ of the D/A converter 50 to the voltage value $DAC_{OUT}[1]$ in Step S11 and drives (i.e., turns on) the light emitting unit 11A by pulse for n frames in Step S12. A frame frequency of the pulse driving in Step S12 is, for example, 100 Hz. In this case, n may be any integer of 1 or more (for example, an integer of 20 or less). In this embodiment, n is 2 or more. One test detection voltage value $V_B$ is obtained for each frame. Thus, n test detection voltage values $V_B$ corresponding to light emission of n frames may be obtained by the pulse driving of Step S12. The light emission controller 34 calculates a voltage value $V_{BB}$, which is a statistics of the n test detection voltage values $V_B$ in Step S13. Since the test detection voltage value $V_B$ represents the test detection light reception intensity, the voltage value $V_{BB}$ can be considered as being indicative of a statistics $R_{II}$ of n test detection light reception intensities. For example, the voltage value $V_{BB}$ as the statistics corresponds to a mean value, a maximum value, a minimum value, a median value, or the mode of the n test detection voltage values $V_B$ (the same for $R_{II}$). For n=1, one test detection voltage value $V_B$ obtained in Step S12 corresponds to the voltage value $V_{BB}$ (the same for $R_{II}$).

Then, in Step S14, the light emission controller 34 compares the voltage value $V_{BB}$ with a reference voltage value $V_{REF}$. If a judgment inequality "$V_{BB} \leq V_{REF}$" is established, the process proceeds to Step S16. On the other hand, if the judgment inequality "$V_{BB} \leq V_{REF}$" is not established, the process proceeds to Step S15. It is here noted that the voltage values $V_B$ and $V_{BB}$ decrease with increase of the light receiving intensity, as described above with reference to FIG. 6. The light receiving intensity for $V_B = V_{REF}$ is referred to as reference light reception intensity. Then, a comparison between the voltage value $V_{BB}$ and the reference voltage value $V_{REF}$ is equivalent to a comparison between the light receiving intensity $R_{II}$ and a predetermined reference light reception intensity $R_{REF}$ while the establishment of the judgment inequality "$V_{BB} \leq V_{REF}$" is equivalent to establishment of "$R_{II} \geq R_{REF}$." That is, if the test detection light reception intensity is equal to or larger than the reference light reception intensity $R_{REF}$, the process proceeds to Step S16. Otherwise, the process proceeds to Step S15.

In Step S15, the light emission controller 34 can increase the output voltage value $DAC_{OUT}$ of the D/A converter 50 by one step and then, the process returns to Step S12. That is, when the process reaches Step S15 in a condition where the current voltage value $DAC_{OUT}$ is a voltage value $DAC_{OUT}[i]$, the voltage value $DAC_{OUT}$ can be increased to a voltage value $DAC_{OUT}[i+1]$ in Step S15.

In Step S16, the light emission controller 34 stores an adjustment voltage value based on the current voltage value $DAC_{OUT}$ or an adjustment voltage value based on a previous voltage value $DAC_{OUT}$, and terminates the adjustment process. In this case, the adjustment voltage value may be stored in a nonvolatile memory (e.g., EEPROM) in the memory 33. When the current voltage value $DAC_{OUT}$ is $DAC_{OUT}[i]$, the previous voltage value $DAC_{OUT}$ is $DAC_{OUT}[i-1]$. Typically, the adjustment voltage value is the current voltage value $DAC_{OUT}$ itself or the very previous voltage value $DAC_{OUT}$ in Step S16 itself. However, a value obtained by adding an additional value $\Delta$ to the current or previous voltage value $DAC_{OUT}$ in Step S16 may correspond to the adjustment voltage value. The additional value $\Delta$ may be either positive or negative. The additional value $\Delta$ may be a predetermined fixed value. The light emission controller 34 may determine the additional value $\Delta$ based on a difference ($V_{REF} - V_{BB}$) in the step where the relationship of "$V_{BB} \leq V_{REF}$" is established.

In the actual detection period after completion of the adjustment process, the light emission controller 34 performs detection of the pulse wave by causing the light emitting unit 11A to emit light under a state where the adjustment voltage value stored in the memory 33 is set to a voltage value $DAC_{OUT}$. A light emission intensity under the state where the adjustment voltage value is set to the voltage value $DAC_{OUT}$ corresponds to the normal light emission intensity (see FIG. 7).

As described above, in this embodiment, the normal light emission intensity is set using the test detection light reception intensity observed by the detection of $V_B$ and the predetermined reference light reception intensity $R_{REF}$. $R_{REF}$ is an expected value of a light receiving intensity to allow the amplitude of the pulse wave signal to be optimized in the actual detection period. Thus, this setting can provide optimization of the amplitude of the pulse wave signal in the actual detection period. In addition, a time required for the amplitude adjustment may be shorter than that in the above-described amplitude actual detection method. For example, if the cycle of the pulse wave is 1 Hz, the amplitude actual detection method typically requires time of 2 to 3 seconds when it determines the amplitude of the pulse wave signal with one light emission intensity. In order to obtain the optimal light emission intensity, the amplitude actual detection method requires time of (m×2) to (m×3) seconds when it determines the amplitude of the pulse wave signal with m light emission intensities. On the other hand, according to this embodiment, for example, if the frame frequency is 100 Hz and (n, m)=(10, 16), the adjustment process is completed in 1.6 (=0.01×10×16) seconds at most.

In order to ensure that the amplitude adjustment is completed in a short time, the length of a period (i.e., FR×n), during which light is emitted from the light emitting unit 11A with each of a plurality of test light emission intensities may be set to be shorter than the cycle of the pulse wave (or the length of a predetermined period expected as the cycle of the pulse wave). For example, the length of the period (FR×n) may be set to 0.5 second or less. In order to promote a rapid amplitude adjustment, a total length of periods, during which light is emitted from the light emitting unit 11A with a plurality of test light emission intensities, may be set to be shorter than the cycle of the pulse wave (or the length of a predetermined period expected as the cycle of the pulse wave). For example, the total length of periods may be set to 0.5 second or less. In this case, the plurality of test light emission intensities refers to two or more test light emission intensities in the adjustment process. In the example of the first embodiment, the plurality of test light emission intensities may be m test light emission intensities. The total length of periods, during which light is emitted from the light emitting unit 11A with the m test light emission intensities, is "FR×n×m."

In the test period, by sequentially changing the voltage value $DAC_{OUT}$, light is emitted from the light emitting unit 11A with a plurality of different test light emission intensities. The above-described flowchart employs a method of increasing the voltage value $DAC_{OUT}$ stepwise until the voltage value $V_{BB}$ becomes equal to or less than the reference voltage value $V_{REF}$ (i.e., until the test detection light reception intensity becomes equal to or greater than the reference light reception intensity). That is, in the above-described adjustment process, sequential light emission with the plurality of test light emission intensities is implemented by the process of increasing the test light emission intensity stepwise. The normal light emission intensity and the adjustment voltage value are set based on the test light emission intensity and the voltage value $DAC_{OUT}$ immediately before or after the test detection light reception intensity $R_H$ is switched from below the reference light reception intensity $R_{REF}$ to the reference light reception intensity $R_{REF}$ or more in the course of the process of increasing the test light emission intensity. More specifically, the adjustment voltage value is set based on the voltage value $DAC_{OUT}$ after the switching (i.e., "the current voltage value $DAC_{OUT}$" in Step S16) or the voltage value $DAC_{OUT}$ before the switching (i.e., "the previous voltage value $DAC_{OUT}$" in Step S16). The normal light emission intensity is determined by setting the adjustment voltage value to the voltage value $DAC_{OUT}$ during the actual detection period.

However, if the judgment inequality "$V_{BB} \leq V_{REF}$" is established under the state where the voltage value $DAC_{OUT}$ is the voltage value $DAC_{OUT}[1]$, i.e., if the test detection light reception intensity $R_H$ when light is emitted from the light emitting unit 11A with the minimum test light emission intensity corresponding to the voltage value $DAC_{OUT}[1]$ is equal to or greater than the reference light reception intensity $R_{REF}$, the process of increasing the test light emission intensity is stopped without performing Step S15 once and the adjustment voltage value is set based on the voltage value $DAC_{OUT}[1]$ (i.e., the normal light emission intensity is set based on the minimum test light emission intensity). How to set the adjustment voltage value based on the voltage value $DAC_{OUT}[1]$ is as described in Step S16.

Although different from the above-described operation, the adjustment process may employ a method of decreasing the voltage value $DAC_{OUT}$ stepwise until the voltage value $V_{BB}$ becomes equal to or more than the reference voltage value $V_{REF}$ (i.e., until the test detection light reception intensity becomes equal to or less than the reference light reception intensity). In this method, $DAC_{OUT}[n]$ is set to $DAC_{OUT}$ in Step S11, a judgment inequality "$V_{BB} \geq V_{REF}$" (i.e., "$R_H \leq R_{REF}$") is used in Step S14, and the voltage value $DAC_{OUT}$ is decreased by one step in Step S15. Thus, if the current voltage value $DAC_{OUT}$ is $DAC_{OUT}[i]$, the previous voltage value $DAC_{OUT}$ in Step S16 is $DAC_{OUT}[i+1]$. That is, in the adjustment process employing the method of decreasing the voltage value $DAC_{OUT}$, sequential light emissions with the plurality of test light emission intensities are implemented by the process of decreasing the test light emission intensity stepwise. The normal light emission intensity and the adjustment voltage value are set based on the test light emission intensity and the voltage value $DAC_{OUT}$ immediately before or after the test detection light reception intensity is switched from above the reference light reception intensity $R_{REF}$ to the reference light reception intensity $R_{REF}$ or less in the course of the process of decreasing the test light emission intensity. Like the method of increasing the voltage value $DAC_{OUT}$, in the method of decreasing the voltage value $DAC_{OUT}$, the adjustment voltage value is set based on the voltage value $DAC_{OUT}$ after the switching (i.e., "the current voltage value $DAC_{OUT}$" in Step S16) or the voltage value $DAC_{OUT}$ before the switching (i.e., "the previous voltage value $DAC_{OUT}$" in Step S16). The normal light emission intensity may be determined by setting the adjustment voltage value to the voltage value $DAC_{OUT}$ during the actual detection period.

However, if the judgment inequality "$V_{BB} \geq V_{REF}$" is established under the state where the voltage value $DAC_{OUT}$ is the voltage value $DAC_{OUT}[m]$, i.e., if the test detection light reception intensity $R_H$ when light is emitted from the light emitting unit 11A with the maximum test light emission intensity corresponding to the voltage value $DAC_{OUT}[m]$ is equal to or less than the reference light reception intensity $R_{REF}$, the process of decreasing the test light emission intensity is stopped without performing Step S15 once and the adjustment voltage value is set based on the voltage value $DAC_{OUT}[m]$ (i.e., the normal light emission intensity is set based on the maximum test light emission intensity). How to set the adjustment voltage value based on the voltage value $DAC_{OUT}[m]$ is as described in Step S16.

Both of the above-described methods belong to a method of finding a voltage value $DAC_{OUT}$ for obtaining the reference light reception intensity $R_{REF}$ or a light reception intensity close to the reference light reception intensity. Such a method of finding the voltage value $DAC_{OUT}$ may include methods other than the above-described methods. For example, Steps S12 and S13 may be performed with the voltage value $DAC_{OUT}$ that is first set to $DAC_{OUT}[m/2]$, and it may be determined, based on an obtained voltage value $V_{BB}$ and reference voltage value $V_{REF}$, whether to increase or decrease the next voltage value $DAC_{OUT}$ from $DAC_{OUT}[m/2]$. As another example, after performing Steps S12 and S13 with the voltage value $DAC_{OUT}$ set to $DAC_{OUT}[1]$, Steps S12 and S13 may be performed with the voltage value $DAC_{OUT}$ set to $DAC_{OUT}[m]$. The next voltage value $DAC_{OUT}$ may be determined based on two voltage values $V_{BB}$ obtained in these performing steps and the reference voltage values $V_{REF}$ so that the reference light reception intensity can be early obtained.

In addition, although light attenuation (i.e., absorbance) of the living body 2 is varied during the adjustment process and this variation has an effect on the test detection voltage $V_B$, the magnitude of the variation makes no difference since it is sufficiently smaller than a variation of the test detection voltage $V_B$ due to a variation of the voltage value $DAC_{OUT}$.

The turning-on of the light emitting unit 11A in the actual detection period may be either in a pulse turning-on manner or a regular turning-on manner. For the regular turning-on manner, the driving current IA is always supplied to the light emitting unit 11A by keeping the FET 51 turned on. Although the method of performing the pulse turning-on in the test period has been described above, the turning-on of the light emitting unit 11A in the test period may be regular turning-on. It is, however, noted that the pulse turning-on can increase a signal S/N ratio more largely than that of the regular turning-on.

Figure 11:
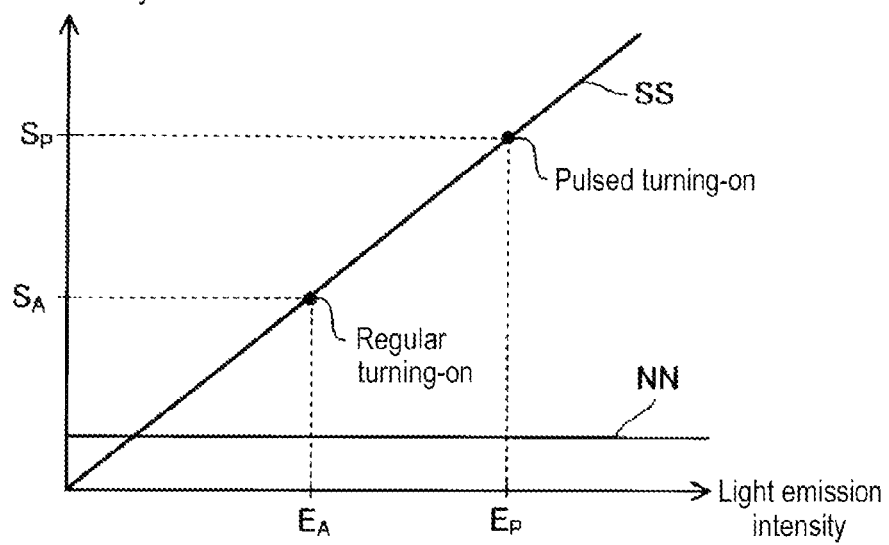

Referring to FIG. 11, a regular turning-on method is compared with a pulse turning-on method. In FIG. 11, a line SS shows a relationship between an instantaneous value of a pulse wave signal intensity and an instantaneous value of a light emission intensity (brightness of the light emitting unit 11A). It is appreciated that the instantaneous value of pulse wave signal intensity should increase with increase of the instantaneous value of a light emission intensity. On the other hand, a line NN shows a noise intensity, which can be considered as being basically constant.

It is assumed that a time average of a light emission intensity in the regular turning-on method is same as that in the pulse turning-on method. Since the instantaneous value of a light emission intensity is always a relatively small intensity $E_A$ in the regular turning-on method, the obtainable maximum pulse wave signal intensity is also a relatively small intensity $S_A$. On the other hand, since the instantaneous value of a light emission intensity in the pulse turning-on is a relatively large intensity $E_P$ ($>E_A$) in the pulse turning-on method, the obtainable maximum pulse wave signal intensity is also a relatively large intensity $S_P$ ($>S_A$). As such, the pulse turning-on method is more likely to increase the instantaneous value of light emission intensity than the regular turning-on method, which can result in improvement of the S/N ratio and make a contribution to extension of a dynamic range.

The adjustment process may be performed at the startup of the pulse wave sensor 1. In addition, the adjustment process may be performed when a specified adjustment execution command is input to the pulse wave sensor 1. An operation input unit (not shown) including mechanical buttons, a touch panel, etc. may be provided to the pulse wave sensor 1, which may receive the adjustment execution command. Alternatively, the external equipment EE may send the adjustment execution command to the pulse wave sensor 1. In addition, for example, after the startup of the pulse wave sensor 1, the adjustment process may be periodically repeatedly performed. In this case, a set period including the test period and the actual detection period is repeated. A voltage value $DAC_{OUT}$ of the actual detection period in a certain set period corresponds to an adjustment voltage value determined during the same set period.

<<Second Embodiment>>

A second embodiment of the present disclosure will be described below. The second embodiment and a third embodiment, which will be described later, are based on the first embodiment. Unless stated specifically in the second and third embodiments and unless contradictory, the description of the first embodiment is applied to the second and third embodiments. Unless contradictory, any combination of the first to third embodiments may be implemented.

Figure 12:
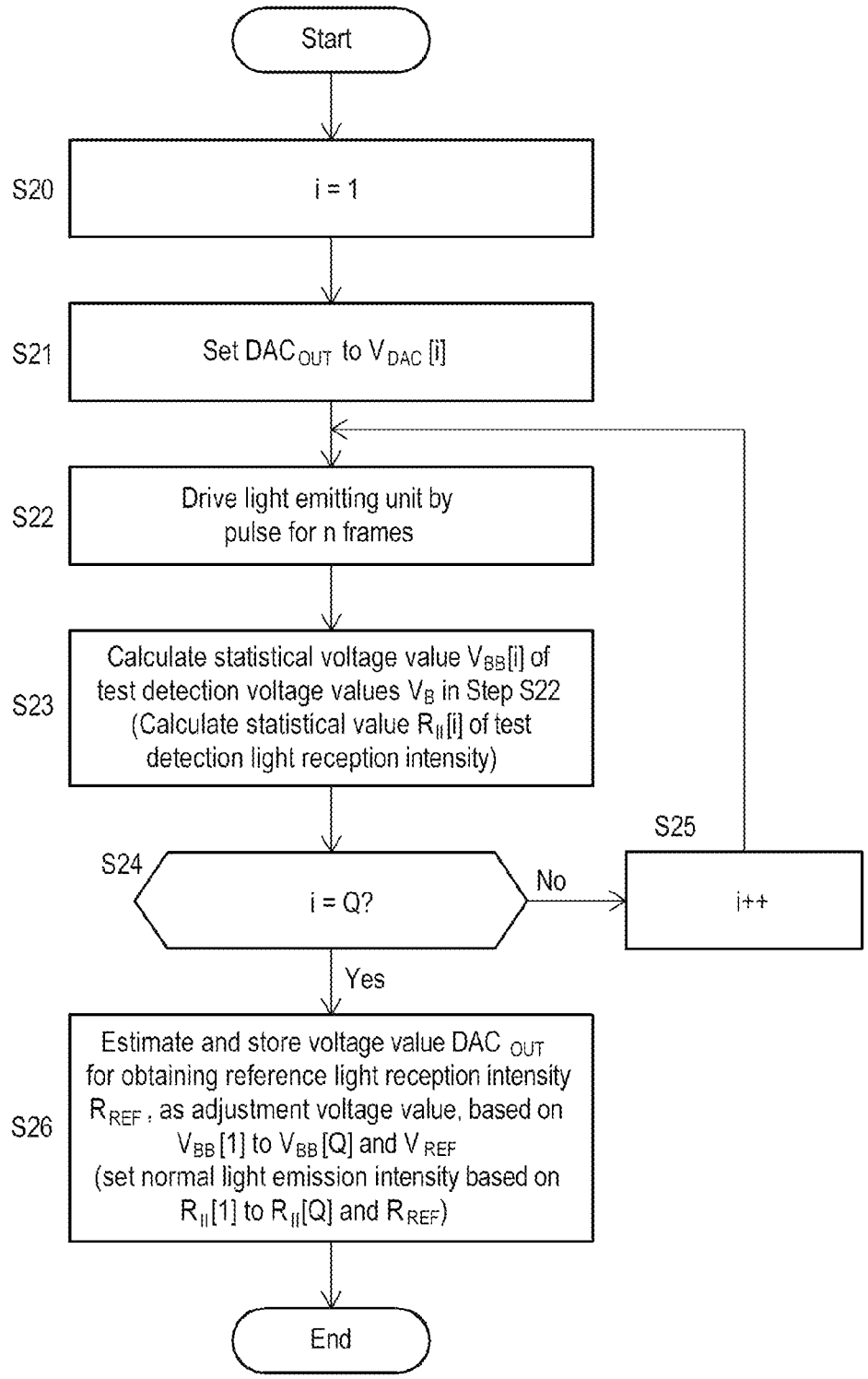
FIG. 12 illustrates a flowchart of an adjustment process according to a second embodiment of the present disclosure.

In the second embodiment, another adjustment process using the above-described pulse wave sensor 1 will be described with reference to FIG. 12. FIG. 12 is a flowchart of an adjustment process including Steps S20 to S26, according to the second embodiment.

The light emission controller 34 first puts 1 in a variable i in Step S20, sets a predetermined voltage value $V_{DAC}[i]$ to the output voltage value $DAC_{OUT}$ of the D/A converter 50 in Step S21, and drives the light emitting unit 11A by pulse for n frames in Step S22. A frame frequency in Step S22 is, for example, 100 Hz. By the pulse driving of Step S22, n test detection voltage values $V_B$ corresponding to light emission of n frames may be obtained. In Step S23, the light emission controller 34 calculates a statistical voltage value $V_{BB}$ of the n test detection voltage values $V_B$ obtained in response to the voltage value $V_{DAC}[i]$, as a voltage value $V_{BB}[i]$. How to calculate the voltage value $V_{BB}$ is as described in the first embodiment. For n=1, one test detection voltage value $V_B$ obtained in Step S22 corresponds to the voltage value $V_{BB}[i]$.

In Step S24, after Step S23 is performed, the light emission controller 34 checks whether or not the variable i is equal to a predetermined value Q. Q is an integer of 2 or more. If the variable i is equal to the predetermined value Q, the process proceeds from Step S24 to Step S26. On the other hand, if the variable i is smaller than the predetermined value Q, 1 is added to the variable i in Step S25 and the process returns to Step S21.

In the steps, before Step S26 is performed, voltage values $V_{BB}[1]$ to $V_{BB}[Q]$ corresponding to $V_{DAC}[1]$ to $V_{DAC}[Q]$ may be obtained. In Step S26, the light emission controller 34 calculates an adjustment voltage value based on the voltage values $V_{BB}[1]$ to $V_{BB}[Q]$ and a predetermined reference voltage value $V_{REF}$, stores the calculated adjustment voltage value in the memory 33, and terminates the adjustment process. An operation performed after the adjustment process is the same as that in the first embodiment.

Figure 13:
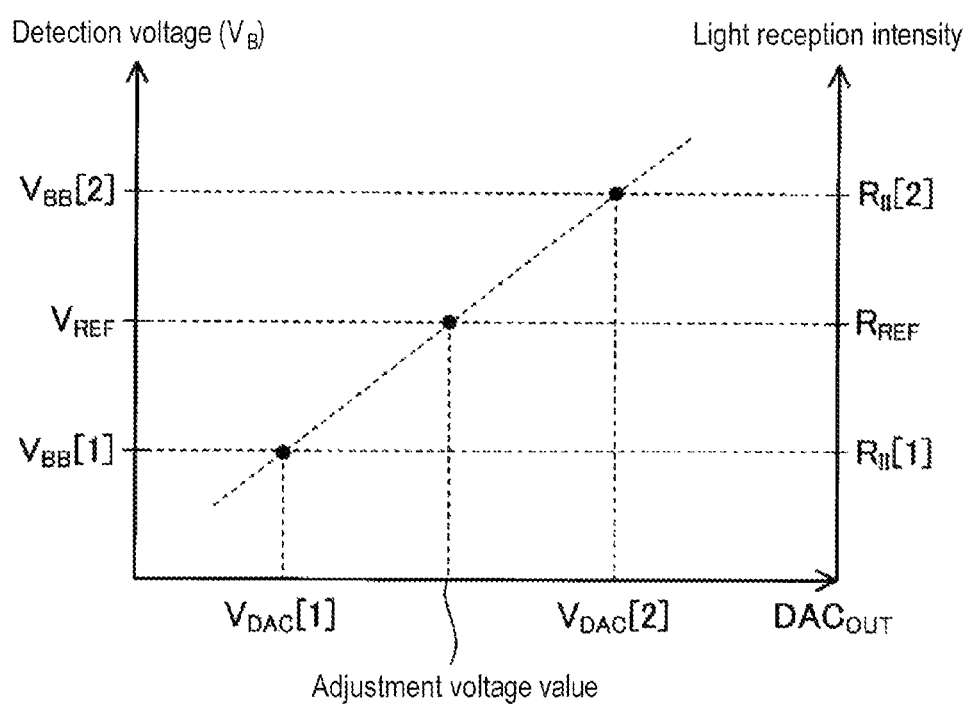
FIG. 13 illustrates how to estimate an adjustment voltage value according to the adjustment process of the second embodiment of the present disclosure.

A method of deriving an adjustment voltage value will now be described with reference to FIG. 13. It is assumed in FIG. 13 that Q is 2. It is also assumed that the test detection voltage value $V_B$ corresponds to the voltage values $V_{BB}[1]$ to $V_{BB}[Q]$ when the voltage value DACOUT corresponds to the predetermined voltage values $V_{DAC}[1]$ to $V_{DAC}[Q]$. In this case, the light emission controller 34 estimates an output voltage value $DAC_{OUT}$ of the D/A converter 50 for setting the voltage value $V_B$ as the reference voltage value $V_{REF}$ and sets the estimated voltage value as an adjustment voltage value. As described above, since light receiving intensity for $V_B=V_{REF}$ is the reference light reception intensity, the output voltage value $DAC_{OUT}$ of the D/A converter 50 for setting the voltage value $V_B$ as the reference voltage value $V_{REF}$ is an output voltage value $DAC_{OUT}$ for obtaining reference light reception intensity $R_{REF}$. The estimation may be implemented by an interpolation process known in the art. As one simple example, if "$|V_{BB}[1]-V_{REF}|=|V_{BB}[2]-V_{REF}|$" and "$V_{BB}[1]<V_{BB}[2]$," "$(V_{DAC}[1]+V_{DAC}[2])/2$" may be set as the adjustment voltage value. A higher value Q can provide higher accuracy of estimation.

In this embodiment, the output voltage value $DAC_{OUT}$ of the D/A converter 50 for setting the detection voltage value $V_B$ (i.e., average level) as the reference voltage value $V_{REF}$ in light emission of the actual detection period is estimated based on the test detection voltage values $V_{BB}[1]$ to $V_{BB}[Q]$ and the reference voltage value $V_{REF}$. The estimated voltage value is set as the adjustment voltage value. In other words, a light emission intensity (corresponding to the adjustment voltage value) for obtaining the reference light reception intensity $R_{REF}$ in the actual detection period is estimated based on the test detection light reception intensities $R_H[1]$ to $R_H[Q]$ corresponding to the test detection voltage values $V_{BB}[1]$ to $V_{BB}[Q]$ and the reference light reception intensity $R_{REF}$ corresponding to the reference voltage value $V_{REF}$. The estimated emission intensity is set as the normal emission intensity. $R_{REF}$ is an expected value of light receiving intensity to allow the amplitude of the pulse wave signal to be optimized in the actual detection period. Thus, this setting may provide optimization of the amplitude of the pulse wave signal in the actual detection period.

The method of the first embodiment is also a kind of method for performing the estimation. That is, in the first embodiment, a light emission intensity (corresponding to the adjustment voltage value) for obtaining the reference light reception intensity $R_{REF}$ in the actual detection period is estimated based on a plurality of test detection light reception intensities (for example, three test detection light reception intensities $R_H$ corresponding to $DAC_{OUT}[1]$ to $DAC_{OUT}[3]$), which is observed in response to a plurality of test light emission intensities, and the reference light reception intensity $R_{REF}$. The estimated light emission intensity is set as the normal light emission intensity. The adjustment voltage value refers to an expression of a result of the estimation in the output voltage value of the D/A converter 50.

A time required for the amplitude adjustment may be shorter than that in the above-described amplitude actual detection method. In order to ensure that the amplitude adjustment is completed in a short time, the length of a period (i.e., FR×n), during which light is emitted from the light emitting unit 11A with each of Q test light emission intensities, may be set to be shorter than the cycle of the pulse wave (or the length of a predetermined period expected as the cycle of the pulse wave). For example, the length of a period (FR×n) may be set to 0.5 second or less. In order to promote a rapid amplitude adjustment, the total length of periods, during which light is emitted from the light emitting unit 11A with Q test light emission intensities, may be set to be shorter than the cycle of the pulse wave (or the length of a predetermined period expected as the cycle of the pulse wave). For example, the total length of periods may be set to 0.5 second or less.

<<Third Embodiment>>

A third embodiment of the present disclosure will be described below. In the third embodiment, still another adjustment process using the above-described pulse wave sensor 1 will be described with reference to FIG. 14. FIG. 14 is a flowchart of an adjustment process including Steps S31 to S34, according to the third embodiment.

Steps S31 to S33 are the same as the above-described Steps S21 to S23 with 1 put in the variable i. In the third embodiment, only the voltage value $V_{BB}[1]$ may be obtained as a statistical voltage value of test detection voltage values $V_B$.

In Step S34, the light emission controller 34 calculates an adjustment voltage value based on the test detection voltage value $V_{BB}[1]$ and a predetermined reference voltage value $V_{REF}$, stores the calculated adjustment voltage value in the memory 33, and terminates the adjustment process. An operation performed after the adjustment process is the same as that in the first embodiment.

More specifically, the light emission controller 34 estimates the output voltage value $DAC_{OUT}$ of the D/A converter 50 for setting the detection voltage value $V_B$ (average level) as the reference voltage value $V_{REF}$ in light emission of the actual detection period based on a result of comparison between the test detection voltage value $V_{BB}[1]$ and the reference voltage value $V_{REF}$ and sets the estimated voltage value as the adjustment voltage value. In other words, a light emission intensity (a light emission intensity corresponding to the adjustment voltage value) for obtaining the reference light reception intensity $R_{REF}$ in the actual detection period is estimated based on a result of comparison between the test detection light reception intensity $R_H[1]$ corresponding to the test detection voltage value $V_{BB}[1]$ and the reference light reception intensity $R_{REF}$ corresponding to the reference voltage value $V_{REF}$. The estimated light emission intensity is set as the normal light emission intensity. $R_{REF}$ is an expected value of light receiving intensity to allow the amplitude of the pulse wave signal to be optimized in the actual detection period. Thus, this setting may provide optimization of the amplitude of the pulse wave signal in the actual detection period.

For example, the light emission controller 34 may set a voltage value $(V_{DAC}[1]-V_{ADJ})$ as the adjustment voltage value if "$V_{BB}[1] \leq V_{REF}$" (i.e., "$R_H[1] \geq R_{REF}$")" and may set a voltage value $(V_{DAC}[1]+V_{ADJ})$ as the adjustment voltage value if "$V_{BB}[1] > V_{REF}$" (i.e., "$R_H[1] < R_{REF}$"). $V_{ADJ}$ denotes a predetermined positive voltage. $V_{ADJ}$ may be a fixed voltage value or a variable voltage value, which increases with increase of a difference $|V_{BB}[1]-V_{REF}|$.

In this embodiment, a time required for the amplitude adjustment may be shorter than that in the above-described amplitude actual detection method. In order to ensure that the amplitude adjustment is completed in a short time, the length of a period (i.e., FR×n) during which light is emitted from the light emitting unit 11A with the test light emission intensity may be set to be shorter than the cycle of the pulse wave (or the length of a predetermined period expected as the cycle of the pulse wave). For example, the length of the period (FR×n) may be set to 0.5 second or less. The third embodiment provides one kind of test light emission intensity and thus has an advantage in that the adjustment process is completed in a shorter time than the first and second embodiments. However, since only a response to the one kind of test light emission intensity is observed, there is a possibility that the adjustment accuracy of the normal light emission intensity (amplitude adjustment accuracy of the pulse wave signal) is coarser than those in the first and second embodiments.

<<Modifications>>

The embodiments of the present disclosure may be modified in various ways within the scope of technical ideas set forth in the claims. The disclosed embodiments are illustrative only and meanings of terms of the present disclosure and its features are not limited to those described in the embodiments. Detailed numerals shown in the description are just examples and, as a matter of course, may be changed in different ways. In the mathematical expressions described in the description, unless contradictory, an inequality sign "≥" or "≤" may be replaced with an inequality sign ">" or "<" and vice versa. Notes 1 to 3 which can be applied to the above-described embodiments will be described below. Unless contradictory, any combination of contents of Notes 1 to 3 may be implemented.

[Note 1]

The number of light emitting elements (such as LEDs, etc.) forming the light emitting unit 11A and the number of light receiving elements (such as photo transistors, etc.) forming the light receiving unit 11B may be optional. For a plurality of light receiving elements, the sum of currents flown in the plurality of light receiving elements may be the current $I_B$ (see FIG. 4).

[Note 2]

The calculator 32, the memory 33, and the light emission controller 34 may be incorporated in the external equipment EE (see FIG. 3) rather than the pulse wave sensor 1. That is, the above-described operations in the calculator 32, the memory 33, and the light emission controller 34 may be implemented within the external equipment EE. Some of the above-described operations in the calculator 32, the memory 33, and the light emission controller 34 may be performed within the pulse wave sensor 1 while the other operations may be performed within the external equipment EE.

[Note 3]

An object device corresponding to the pulse wave sensor 1 may be implemented with hardware such as integrated circuits, or a combination of hardware and software. Some or all specific functions implemented in the object device may be written as programs, which may be stored in a flash memory installable in the object device. The specific functions may be implemented by executing the programs on a program executing device (for example, a microcomputer installable in the object device). The programs may be stored and fixed in any recording medium, which may be installed in or connected to a device (such as a server, etc.) other than the object device.

According to the present disclosure in some embodiments, it is possible to provide a pulse wave sensor, which is capable of optimizing a light emission intensity for detection of a pulse wave in a short time.

While certain embodiments have been described, these embodiments have been presented by way of example only, and are not intended to limit the scope of the disclosures. Indeed, the novel methods and apparatuses described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A pulse wave sensor comprising:
a light emitter installed in a housing and configured to emit light onto a living body;
a light receiver installed in the housing and configured to receive light which is transmitted through or is reflected from the living body based on the light from the light emitter;
a pulse wave detector configured to detect a pulse wave of the living body based on a result of light reception by the light receiver when the light is emitted from the light emitter with a normal light emission intensity; and
a light emission intensity controller configured to cause the light emitter to perform light emission with a predetermined test light emission intensity in a test period prior to the detection of the pulse wave, set the normal light emission intensity using a detection light reception intensity in the light receiver by the light emission during the test period and a predetermined reference light reception intensity, and cause the light emitter to emit light with the normal light emission intensity during detection of the pulse wave.

2. The pulse wave sensor of claim 1, wherein the light emission intensity controller is configured to cause the light emitter to sequentially emit light with a plurality of different test light emission intensities in the test period, and set the normal light emission intensity using a plurality of detection light reception intensities in the light receiver that correspond to the plurality of test light emission intensities and the predetermined reference light reception intensity.

3. The pulse wave sensor of claim 2, wherein the light emission intensity controller is configured to implement sequential light emission with the plurality of test light emission intensities according to a process of increasing a light emission intensity of the light emitter stepwise, and set the normal light emission intensity based on one of the plurality of test light emission intensities before or after one of the plurality of detection light reception intensities, which corresponds to the one of the plurality of test light emission intensities, is switched from below the reference light reception intensity to the reference light reception intensity or more in a course of the process of increasing the light emission intensity, or
wherein the light emission intensity controller is configured to implement sequential light emission with the plurality of test light emission intensities according to a process of decreasing a light emission intensity of the light emitter stepwise, and set the normal light emission intensity based on one of the plurality of test light emission intensities before or after one of the plurality of detection light reception intensities, which corresponds to the one of the plurality of test light emission intensities, is switched from above the reference light reception intensity to the reference light reception intensity or less in a course of the process of decreasing the light emission intensity.

4. The pulse wave sensor of claim 3, wherein the light emission intensity controller is configured to first cause the light emitter to emit light with a smallest test light emission intensity of the plurality of test light emission intensities, stop the process of increasing the light emission intensity when a detection light reception intensity of the plurality of the detection light reception intensities, which corresponds to the smallest test light emission intensity, is equal to or larger than the reference light reception intensity, and set the normal light emission intensity based on the smallest test light emission intensity, or
wherein the light emission intensity controller is configured to first cause the light emitter to emit light with a greatest test light emission intensity of the plurality of test light emission intensities, stop the process of decreasing the light emission intensity when a detection light reception intensity of the plurality of the detection light reception intensities, which corresponds to the greatest test light emission intensity, is equal to or less than the reference light reception intensity, and set the normal light emission intensity based on the greatest test light emission intensity.

5. The pulse wave sensor of claim 3, wherein the light emission intensity controller sets a value, which is obtained by adding an additional value to the one of the plurality of test light emission intensities before or after the corresponding one of the plurality of detection light reception intensities is switched from below the reference light reception intensity to the reference light reception intensity or more in the course of the process of increasing the light emission intensity, as the normal light emission intensity, or
wherein the light emission intensity controller sets a value, which is obtained by adding an additional value to the one of the plurality of test light emission intensities before or after the corresponding one of the plurality of detection light reception intensities is switched from above the reference light reception intensity to the reference light reception intensity or less in the course of the process of decreasing the light emission intensity, as the normal light emission intensity.

6. The pulse wave sensor of claim 5, wherein the light emission intensity controller determines the additional value based on a difference between the reference light reception intensity and the one of the plurality of test light emission intensities before or after the corresponding one of the plurality of detection light reception intensities is switched from below the reference light reception intensity to the reference light reception intensity or more in the course of the process of increasing the light emission intensity, or wherein the light emission intensity controller determines the additional value based on a difference between the reference light reception intensity and the one of the plurality of test light emission intensities before or after the corresponding one of the plurality of detection light reception intensities is switched from above the reference light reception intensity to the reference light reception intensity or less in the course of the process of decreasing the light emission intensity.

7. The pulse wave sensor of claim 2, wherein the light emission intensity controller is configured to estimate a light emission intensity for obtaining the reference light reception intensity based on the plurality of detection light reception intensities and the reference light reception intensity, and set the normal light emission intensity based on the estimated light emission intensity.

8. The pulse wave sensor of claim 7, wherein the light emission intensity controller estimates the light emission intensity for obtaining the reference light reception intensity by an interpolation process.

9. The pulse wave sensor of claim 2, wherein a length of a period, during which light is emitted from the light emitter with each of the plurality of test light emission intensities, is set to be shorter than a cycle of the pulse wave or is set to 0.5 second or less.

10. The pulse wave sensor of claim 9, wherein a total length of periods, during which light is emitted from the light emitter with the plurality of test light emission intensities, is set to be shorter than the cycle of the pulse wave or is set to 0.5 second or less.

11. The pulse wave sensor of claim 2, wherein the light emission intensity controller is configured to implement sequential light emission with the plurality of test light emission intensities by first causing the light emitter to emit light with a median one of the plurality of test light emission intensities and determining whether to increase or decrease a light emission intensity of the light emitter stepwise from the median one of the plurality of test light emission intensities.

12. The pulse wave sensor of claim 2, wherein the light emission intensity controller is configured to implement sequential light emission with the plurality of test light emission intensities by causing the light emitter to sequentially emit light with a smallest one of the plurality of test light emission intensities and light with a greatest one of the plurality of test light emission intensities, and determining a next one of the plurality of test light emission intensities.

13. The pulse wave sensor of claim 1, wherein the test light emission intensity is a predetermined single light emission intensity, and wherein the light emission intensity controller is configured to set the normal light emission intensity based on a result of comparison between the detection light reception intensity and the reference light reception intensity.

14. The pulse wave sensor of claim 13, wherein the light emission intensity controller is configured to:

obtain a light intensity by subtracting a predetermined value from the test light emission intensity when the detection light reception intensity is equal to or greater than the reference light reception intensity and by adding the predetermined value to the test light emission intensity when the detection light reception intensity is smaller than the reference light reception intensity; and set the light intensity as the normal light emission intensity.

15. The pulse wave sensor of claim 14, wherein the predetermined value is a variable value which increases with increase of a difference between the detection light reception intensity and the reference light reception intensity.

16. The pulse wave sensor of claim 1, wherein a length of a period during which light is emitted from the light emitter with the test light emission intensity is set to be shorter than a cycle of the pulse wave or is set to 0.5 second or less.

17. The pulse wave sensor of claim 1, wherein the light emission intensity controller is configured to turn on the light emitter by pulse with the test light emission intensity in the test period.

18. The pulse wave sensor of claim 1, wherein the light emitter and the light receiver are disposed on the same side of the housing with respect to the living body.

19. The pulse wave sensor of claim 1, wherein the light emitter and the light receiver are disposed on opposite sides of the housing with the living body interposed therebetween.

* * * * *